United States Patent
Wolfson

(10) Patent No.: US 9,265,528 B2
(45) Date of Patent: Feb. 23, 2016

(54) ORTHOPEDIC FIXATION SYSTEMS AND METHODS

(76) Inventor: Nikolaj Wolfson, San Francisco, CA (US)

( * ) Notice: Subject to any disclaimer, the term of this patent is extended or adjusted under 35 U.S.C. 154(b) by 0 days.

(21) Appl. No.: 12/956,768

(22) Filed: Nov. 30, 2010

(65) Prior Publication Data

US 2012/0136355 A1    May 31, 2012

(51) Int. Cl.
*A61B 17/66* (2006.01)
*A61B 17/62* (2006.01)
*A61B 17/64* (2006.01)
*A61B 17/84* (2006.01)

(52) U.S. Cl.
CPC ............. *A61B 17/62* (2013.01); *A61B 17/6408* (2013.01); *A61B 17/645* (2013.01); *A61B 17/6441* (2013.01); *A61B 17/846* (2013.01)

(58) Field of Classification Search
CPC ............ A61B 17/62–17/66; A61F 5/04–5/048
USPC .................... 606/54–59; 602/32–40
See application file for complete search history.

(56) References Cited

U.S. PATENT DOCUMENTS

| | | | |
|---|---|---|---|
| 661,812 A | 11/1900 | McKown et al. | |
| 2,020,262 A | 11/1935 | Longfellow | |
| 2,032,653 A * | 3/1936 | Ettinger | 602/39 |
| 2,035,952 A | 3/1936 | Ettinger | |
| 2,079,567 A | 5/1937 | Anderson | |
| 2,080,802 A | 5/1937 | Anderson | |
| 2,101,889 A | 12/1937 | Anderson | |
| 2,120,446 A * | 6/1938 | Thomas | 606/56 |
| 2,185,322 A | 1/1940 | Anderson | |
| 2,204,266 A | 6/1940 | Wilcox | |
| 2,214,490 A | 9/1940 | Thomas | |
| 2,238,869 A | 4/1941 | Haynes | |
| 3,727,610 A | 4/1973 | Riniker | |
| 4,006,740 A * | 2/1977 | Volkov et al. | 606/53 |
| 4,365,624 A | 12/1982 | Jaquet | |
| 4,535,763 A * | 8/1985 | Jaquet | 606/56 |
| 4,628,922 A * | 12/1986 | Dewar | 606/56 |
| 4,779,857 A * | 10/1988 | Maund | B25H 1/0042 144/48.3 |
| 5,403,319 A * | 4/1995 | Matsen et al. | 606/88 |
| RE34,985 E * | 6/1995 | Pennig | A61B 17/6416 606/57 |
| 5,439,465 A * | 8/1995 | Tumibay | A61B 17/6408 606/105 |
| 5,496,319 A * | 3/1996 | Allard et al. | 606/56 |
| 5,863,292 A * | 1/1999 | Tosic | 606/56 |

(Continued)

OTHER PUBLICATIONS

Pichkhadze, Issak M., MD, PhD, "Pichkhadze's Apparatus for Monopolar, Bipolar and Polypolar Stabilziation and Ability to Assemble (Align) the Bone Fragments in 3D," 2002 [retrieved on May 7, 2010]. Retrieved from the Internet< URL: http://www.orthopaed-rmp.ru/3_3e.html>.

*Primary Examiner* — Jacqueline Johans

(57) ABSTRACT

The invention provides an orthopedic external fixation system for treatment of lower and upper extremities fractures. The system comprises an elongate base rail supported by a stand structure and a plurality of open rings slidably and removably coupled to the base rail along the base rail length. The ring members are connected to struts that support flag members, which support wires and pins that interact with the fractured bones for fixation of their positions relative to the rings during treatment. The system has means for combining the rings into separate modules that can be moved relative to each other. Through the use of the struts the rings can be bound into an integral system that can be disconnected from the base and the stand structure, while remains in a working position on the injured limb of the patient.

6 Claims, 12 Drawing Sheets

(56) References Cited

U.S. PATENT DOCUMENTS

| | | | |
|---|---|---|---|
| 5,968,043 A * | 10/1999 | Ross et al. | 606/56 |
| 5,979,658 A * | 11/1999 | Allen et al. | 206/572 |
| 6,328,737 B1 | 12/2001 | Moorcroft et al. | |
| 6,860,883 B2 * | 3/2005 | Janowski et al. | 606/56 |
| 7,662,159 B2 * | 2/2010 | Brandigi | 606/108 |
| 8,172,849 B2 * | 5/2012 | Noon et al. | 606/90 |
| 2003/0009167 A1 * | 1/2003 | Wozencroft | 606/55 |
| 2005/0043730 A1 * | 2/2005 | Janowski et al. | 606/56 |
| 2005/0113829 A1 * | 5/2005 | Walulik et al. | 606/54 |
| 2005/0251136 A1 * | 11/2005 | Noon et al. | 606/56 |
| 2006/0116619 A1 * | 6/2006 | Weinstein et al. | 602/32 |
| 2007/0055234 A1 | 3/2007 | McGrath et al. | |
| 2008/0086122 A1 * | 4/2008 | Starr | 606/56 |

* cited by examiner

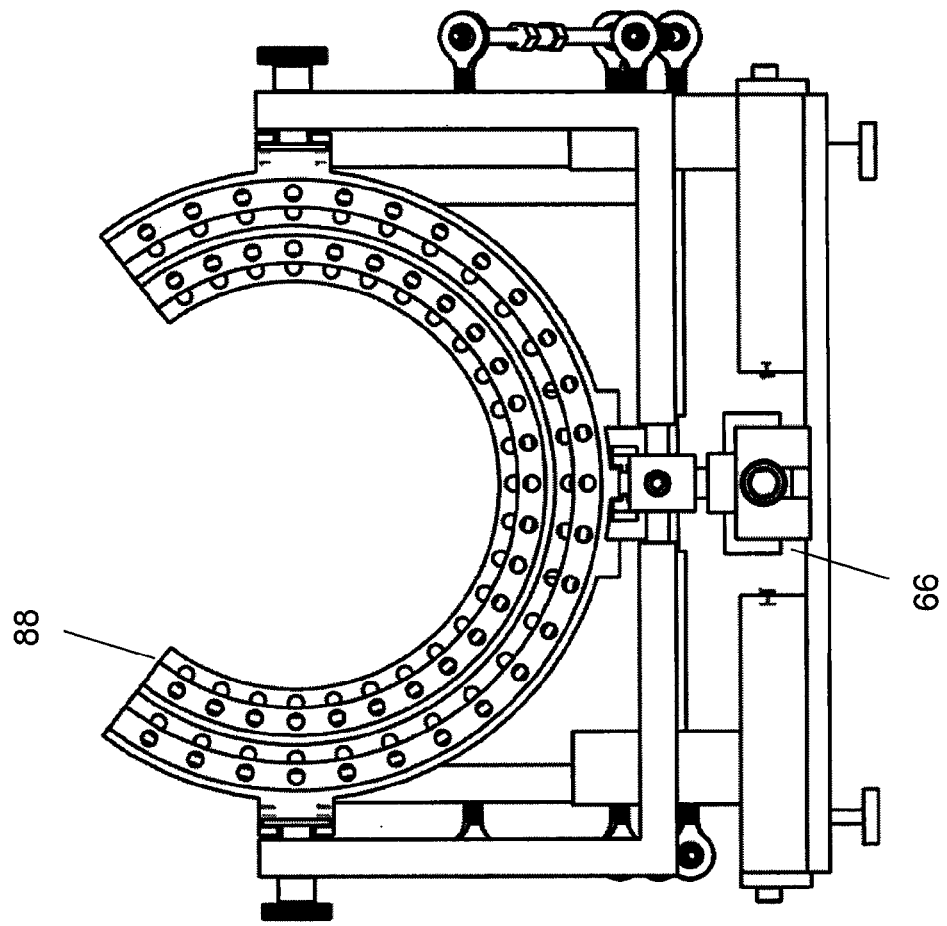
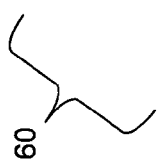
FIG. 10

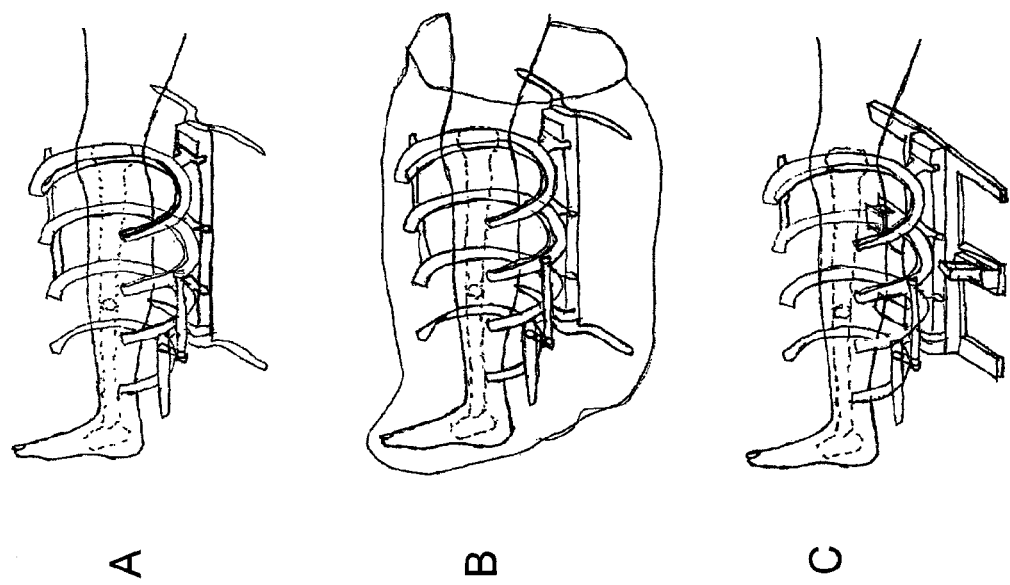

ORTHOPEDIC FIXATION SYSTEMS AND METHODS

BACKGROUND OF THE INVENTION

The present invention relates to orthopedic fixation systems, assemblies, devices and related methods for reduction of a fractured bone of a patient.

Reduction is a medical procedure to restore a fracture or dislocation to the correct alignment. When a bone fractures, the fragments lose their alignment in the form of displacement or angulation. For the fractured bone to heal without substantial deformity the bony fragments must be re-aligned to their normal anatomical position. Orthopedic surgeons attempt to recreate the normal anatomy of the fractured bone by reduction.

Fractured bone reduction or treatment can include use of fixation methods that can reinforce the fractured bone and keep it aligned during healing, including use of external devices or casts as well as internal devices such as rods, bone plates and/or fasteners. Under certain circumstances, a physician may decide that external fixation is the best treatment for a patient. Fixation with external devices and assemblies includes surgical techniques for setting bone fractures and/or for limb lengthening that was first used more than a century ago. Since that time, the technique has evolved from being used primarily as a last resort fixation method to becoming a main stream technique used to treat a myriad of bone and soft tissue pathologies.

In some cases, external fixation can be accomplished by placing pins or screws into the bone of a patient and securing the pins through the use of an external frame assembly positioned at least partially outside the body. During the treatment, the external frame can hold bone fragments at adjustable spacing and angles to create a desired overall bone length and angular disposition of the bone fragments. To connect the external fixation device to the bone, pins can be placed, for example, on either side of the break in the bone and pass through the skin and sometimes the muscles. Sometimes wires can also be used with the pins, or in place of pins, to secure the bone pieces. The pins and/or wires can hold the bone in place and anchor the fixator securely, while also avoiding damage to vital structures, allowing access to the area of injury, and meeting the mechanical demands of the patient and the injury. Treatment using external fixation can take about 6 weeks for a simple fracture, and up to one year or longer for a more complicated fracture.

As compared to other fixation methods, external fixation devices can provide numerous advantages. When compared with internal plates and intramedullary nails, for example, external fixators can cause less disruption of the soft tissues, osseus blood supply, and periosteum. Accordingly, external fixation devices can be useful for soft tissue management in the setting of acute trauma with skin contusions and open wounds, in chronic trauma where the extremity is covered in thin skin grafts and muscle flaps, and in patients with poor skin whose healing potential is compromised as in the case of rheumatoid disease, peripheral vascular disease, diabetes mellitus, and Charcot disease. In addition, the temporary nature of the pins and wires can provide bony stability in the setting of osteomyelitis where the presence of internal implants make eradication of infection more challenging. The ability to avoid putting fixation into the infected area is equally beneficial.

Unlike internal plates and intramedullary nails, external fixators also provide postoperative adjustability. This allows the extremity to be manipulated in the operating room to gain exposures to fracture fragments. In the situation of limb lengthening or deformity correction, gradual manipulation is possible with frame adjustment over time. As a result, external fixations have found use in pediatric fracture care where open physes preclude intramedullary nailing. Leg length discrepancy can also be reliably treated with circular and monolateral design fixators.

Despite these advantages, existing external fixation devices and assemblies still remain limited in their application for treatment of bone fractures. For example, while the devices known in the prior art can help provide valuable treatment of fractures, particularly in the surgical setting, existing devices can be somewhat cumbersome and limited in versatility. Thus, there is continued interest in providing improved external fixation devices that are more versatile and can be used, for example, as more ambulatory or portable devices.

BRIEF SUMMARY OF THE INVENTION

The present invention relates to orthopedic fixation systems, assemblies, devices and related methods for reduction of a fractured bone of a patient.

In one embodiment, the present invention provides orthopedic fixation systems including a primary fixation device and a base station. The base station can be configured to receive and reversibly couple with the primary fixation device in whole or in part, for formation of a more elaborate or more stabilized fixation or bone reduction assembly.

Systems further include frame components, e.g., rings, struts, rails, and/or braces, as well as bone-interface components, e.g., pins and/or wires. The frame components, for example, can be used by a healthcare provider to assemble the systems in a fashion to allow for varied levels of stabilization. In one embodiment, the primary fixation device can include an elongate base rail having a length and opposing distal and proximal end portions each removably couplable to a stand structure. The primary fixation device can further include one or more rings removably and slidably coupled to the base rail along the base rail length. The base station will generally have a surface stabilizing structure or arrangement, where the base station disposed on a working surface (e.g., surgical setting or table) can couple together with the primary fixation device and provide a stabilized combined assembly. For example, the base station can have a generally "H" shaped base frame that can include an elongate center support having a length and opposing distal and proximal end portions each presenting a lateral support. The systems of the present invention can further include bone-interface components that, for example, can be used to connect to a bone for medical procedures, such as fixation and/or reduction. In one embodiment, the bone-interface components can include fixing pins and wires.

The methods of using the systems of the present invention can include a variety of embodiments. In one embodiment, a method can include transporting a patient from a first point to a second point while the patient's bone is immobilized in a primary fixation device. The primary fixation device, in whole or in part, can be coupled together to a base station at the second point, e.g., while the patient's bone is immobilized.

In another embodiment, the methods can include providing an orthopedic fixation system having a primary fixation device and a base station, and then coupling or uncoupling the primary fixation device and the base station while a bone of a patient is fixed or reduced with the primary fixation device. In yet another embodiment, a method can include fixing or reducing a limb of a patient in a primary fixation device and coupling the primary fixation device to a base station while the patient's limb is constrained with the primary fixation device.

The present invention can further include sterilization kits and methods for sterilizing a patient's limb while immobilized in a fixation device and/or system. The sterilization kits can include a sterilizing container, a sterilization solution, or other parts for a kit that can provide sterilization. In one embodiment, a patient's limb can be sterilized after fixation or reduction of the limb in a primary fixation device by placing a sterilizing container around the limb and the device. The sterilizing container can be removed before or after coupling the primary fixation device to a base station.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 10 illustrates a view down the length of an orthopedic fixation system, according to an exemplary embodiment of the present invention.

FIG. 11A-C illustrate an exemplary method for sterilizing a patient's limb while being stabilized in an assembly of the present invention.

DETAILED DESCRIPTION OF THE INVENTION

Figure 1B:
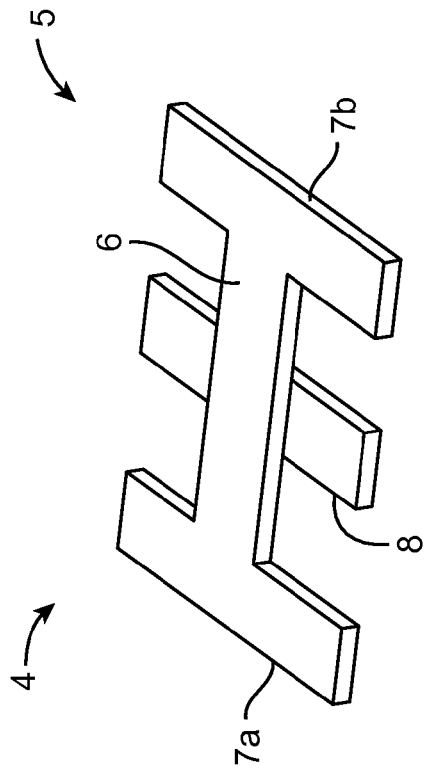
FIGS. 1A-C illustrate a primary fixation device, a base station, and an orthopedic fixation system, in accordance with an exemplary embodiment of the present invention.

The present invention relates to orthopedic fixation systems, assemblies, devices and related methods for fracture reduction or fixation, as well as stabilizing a patient's limb for a reduction procedure.

Fracture reduction or fixation systems as described herein generally reference two main components: a primary fixation device and a base station. The primary fixation device generally includes an elongate base rail with one or more frame or bone-interface components disposed along the rail so as to provide some degree of adjustability or fracture reduction capacity. The base station couples together with the primary fixation device for increased stabilization and/or functionality of the combined assembly.

In use, fracture reduction in a patient may employ fixation system components in both an uncoupled stages as well as a stage where components (e.g., primary fixation device and base assembly) are coupled together during treatment. For example, the primary fixation device may be utilized for a more temporary and/or ambulatory stabilization of a patient, before the patient is transported to a more long-term or less transient setting. After an initial or first stage of reduction/fixation of the patient fracture with the primary fixation device, the device (e.g., in whole or in part) can be coupled together with a base station for further stabilization and fracture reduction. Thus, systems may find use in settings such as an emergency room or field setting, where the patient receives some degree of reduction of the patient with employment of the primary reduction device, followed by coupling of the primary reduction device (e.g., following patient transport or movement) to a surgical setting or operating room for more throughout fracture reduction and treatment.

Orthopedic fixation systems as described herein generally include frame structures that surround and/or extend along one or more bones to allow for stabilization of a fracture and/or reconstruction of bones and/or surrounding tissue. The systems of the present invention can include a variety of components that can be selected for a desired level of stabilization. Systems of the present invention can include at least two main components: a primary fixation device and a base station. As indicated, a primary fixation device can be configured with an elongate base rail and other frame or bone-interface components (e.g., rings and/or fixation pins, respectively) that can assist in stabilizing a bone (e.g., tibia, fibula, femur or humerus). The base station can include a base frame and can be further configured to receive and removably couple with the primary fixation device, which can also be configured to couple with the base station. Coupling the primary fixation device to the base station can be accomplished through a variety of ways. In certain embodiments, the primary fixation device can be wholly coupled to the base station without removing or replacing any components coupled to the primary fixation device. Alternatively, the primary fixation device can be partially coupled with the base station such that some of the components are replaced or modified to provide additional stabilization or other features that may be desired by a healthcare provider. A primary fixation device may initially wholly be coupled together with a base station, followed by adjustment or replacement of components of the primary fixation device.

For use, the systems of the present invention can be generally used for medical procedures that involve fixation and/or reduction of a patient's bone, including limb stabilization. The orthopedic fixation systems of the present invention can be applied to treat various bones or fractures, including bones/fractures of both upper and/or lower limbs, such as a bone in the leg or the arm. A leg bone can include a femur, a tibia, a fibula, or a combination thereof. An arm bone can include a humerus, a radius, an ulna, or a combination thereof. In some embodiments, a segment of a bone can be treated using a device of the present invention. In certain embodiments, the orthopedic fixation systems of the present invention can also serve as reduction devices for a fractured or dislocated bone. For example, the systems can be configured to provide open or closed reduction. For open reduction, bone fragments are exposed surgically to assist in restoring a fracture or dislocation. Closed reduction can manipulate the bone fragments without surgical exposure.

In certain notable aspects, the coupling relationship between the primary fixation device and the base station particularly can allow for increased portability and flexibility for stabilizing a bone, for example, at the scene of an accident or other environments in which portability is desired to keep the bone stabile before surgery in an operating room. The systems can also provide a greater versatility in use because the systems can be assembled to allow for different levels of stabilization of the bone. For example, in some situations, healthcare providers may desire more adjustable systems for mobility that can later be modified to increase stability upon arrival to a location that allows for such modifications. As described in more detail below, a primary fixation device can be assembled to include frame components that may allow for fixation or reduction of a bone in situations that involve more temporary, mobile stabilization. Upon initial treatment of a patient, the stabilization device can provide less stability, and thus better portability, than, e.g., the greater stability that may be desired for some operating room situations.

The orthopedic fixation systems described herein can include one or more of a variety of components for the primary fixation device and/or base station. As noted, systems typically form a frame-like assembly that is worn or disposed outside the body and along the bone or fracture site. Thus, systems herein will include certain frame structures or components, such as, e.g., rings, rails, braces, struts, arms, etc. Systems will often make use of stabilization or fixation rings, which can couple to other system components (e.g., base rail) for formation of a frame-like structure and facilitate stabilization of a bone in a reduction procedure. In one embodiment, frame components of a primary fixation device will include one or more rings each coupled along an elongate base rail.

In addition to frame components, the systems can further include certain components for interfacing between the system outer frame structure and the patient's bone or fragments ("bone-interface components") to allow manipulation, positioning, or re-alignment of bone fragments for reduction. Bone interface components can include, for example, various types of orthopedic pins, rods, screws, shafts, wires, and the like that can connect to a bone, e.g., between a frame component and the patient's bone/fragment for positioning or reduction as described. Bone-interface components are commonly coupled to frame ring structures and can be coupled to various frame components, including rings, struts, rails, arms, etc.

As described herein, the systems can include a multitude of frame components, such as rings and base rails. The rings can be of any size and/or shape suitable for use with the systems, devices, and methods of the present invention. The rings can include full rings and/or partial rings, such as half or three-quarter rings, and/or U-shaped plates. Rings can further include mechanisms for mounting other bone-interface components. For example, rings can include holes or ribs that can be coupled with additional mounting components, such as brackets or other structures that allow for coupling connectors to interface with bone. In certain embodiments, the rings can be removably and/or slidably coupled to an elongate base rail of a primary fixation device. Coupling of the rings to the base rail can be achieved using several different mechanisms, and the base rails of the primary fixation devices can be of any suitable size or shape. In some embodiments, a base block or other slidable structure that fits to the base rail can slide along the length of the rail so as to allow horizontal placement of the rings in relation to a bone. Once in a desired position, the base block can be tightened to the base rail to remain in the desired position. Relative height of the rings in relation to the base rail can be further adjusted with an adjustable pedestal that can couple with the ring. The adjustable pedestal can further removably and/or slidably couple to a base block via a post, and the pedestals can slide along the posts to adjust the height of the ring in a direction that is, e.g., orthogonal to the length of the base rail. Similar to the base block, the pedestals can be held in a rigid position by a variety of mechanisms, such as screw tightening. In certain embodiments, the rings can be further supported by ring supports that can couple to the base rail or the base station. The ring supports, for example, can be used after the primary fixation device is coupled to the base station and a healthcare provider desires increased stabilization.

Struts used in the present invention may have any suitable dimension of size or shape to, for example, provide for stabilization and/or mounting of various bone-interface components or other frame components. Struts can be elongate and substantially linear in shape or a whole or part of the strut can be bent (e.g., angular and/or curved). In some embodiments, a strut can be a member of a set of struts, in which each strut can be the same size or of different sizes. The set of struts can include struts of the same and/or different diameter, the same and/or different maximum (and/or minimum) length, and/or the same and/or different angular adjustability. Distinct struts, of the same or different size/adjustability, can be marked as distinct. For example, the struts may include indicia, such as alphanumeric characters, distinct colors, removable (or permanent) colored bands, etc. In some embodiments, the indicia can be used by a healthcare professional to choose specific struts having a desired shape and/or stiffness for a particular stabilization procedure. In certain embodiments, struts can also include one or more movable joints that can, e.g., permit relative (internal) translational or pivotal motion of portions the strut. In some embodiments, the joint can allow a twisting motion about an axis parallel to a long axis defined by the strut. In addition, a joint can also permit a bending motion(s) about an axis (or axes) transverse to the long axis of the strut. The joint may be a hinge joint, a ball-and-socket joint, and/or a combination thereof, among others.

The struts can be secured by any suitable mechanism to primary fixation devices, base stations, rings, other struts, or other components of the systems of the present invention. For example, a strut can be fastened at several points along a set of rings that are removably and slidably coupled to an elongate base rail of a primary fixation device. Alternatively, one strut can be coupled at one end to one ring and at the other end to a second ring. The locations and orientations of the struts in relation to rings, or other components, can be dependent on the particular application of the struts for stabilizing the bone in an orthopedic fixation system of the present invention.

Additional support components, such as braces, can be coupled to the base station, the primary fixation device, and/or other components so as to increase or decrease the stabilization level of the orthopedic fixation systems. In certain embodiments, the braces can provide additional stabilization support when a primary fixation device is coupled to a base station. Braces can include various components configured to facilitate support for the systems as well as to provide adjustment capability for a user. Suitable brace components can include rod supports, hinges, adjustment handles, joints, etc. The braces can have a configuration that can be adjusted in a variety of ways, such as in length, angle, height, etc. In some embodiments, the braces can include at least one joint or hinge to permit internal relative motion among various components of the brace. Other components, such as adjustment handles, can be configured to allow a healthcare provider to adjust the size and/or shape of the brace as well as the way the brace can couple with other system components, such as the base station.

In addition to the frame components, base station, and/or primary fixation device, the present invention includes bone-interface components that can be connected to a bone. Suitable bone-interface components can include fixation pins, wires, screws, nails, plates, rods, bolts, staples, hooks, clamps, and the like, and/or a combination thereof. The bone-interface components can extend into bone, through bone, and/or around bone, etc. Furthermore, the bone-interface components can be slidably engaged with bone and/or fixed in relation to bone (e.g., threaded into bone). In some embodiments, the bone-interface components can extend from a frame component, e.g., a ring, to bone, or from a frame component to bone and then back to the same frame component. In other embodiments, a bone-interface component can extend from a frame component to bone and then to a different frame component. Each frame component can be connected to bone via the same or different type of mechanism.

In general, the frame components and/or bone-interface components can be coupled (e.g., permanently or removably coupled) to other components through a variety of ways. The coupling mechanisms for the systems of the present invention can generally include coupling mechanisms, such as fasteners, screws, nuts, brackets, and/or bolts, as well as other ways to attach various components, such as welding, gluing, tying, etc. In addition, rings can be removably and slidably coupled to an elongate base rail of a primary fixation device. Fixing pins and/or wires can be independently and/or removably coupled to the rings. Alternatively, the fixing pins and/or wires can be independently and/or removably coupled to components that are coupled to the rings or to the base. Coupling additional components to various parts of the assembly can depend on several factors, such as the bone needed fixation and/or reduction or, e.g., the placement of a fracture in the bone.

As provided in more detail below, representative aspects of embodiments of systems, devices, components and methods of the present invention are described with reference to the identified figures.

Figure 1A:
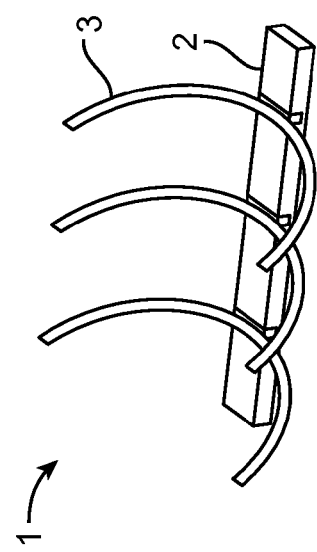
Figure 1C:
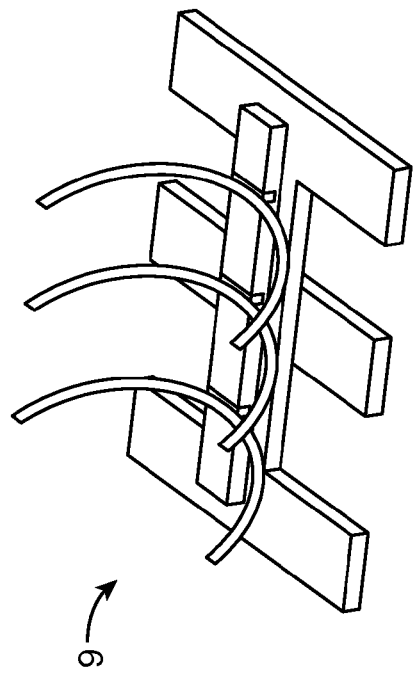

FIGS. 1A-C provide an exemplary orthopedic fixation system of the present invention. As shown in FIG. 1A, the primary fixation device 1 can include an elongate base rail 2 having a length and opposing distal and proximal end portions. One or more rings 3 can be removably and slidably coupled to the base rail 2 along the base rail length. The primary fixation device 1 will enable some degree of fracture reduction capacity, and may include any number of further components such as frame components as well as bone interface components.

A fixation system further includes a base station, that will include one or more surface stabilization components such that the base station coupled together with a primary fixation device can be stably positioned on a surface for fracture reduction and treatment of a patient. As depicted in FIG. 1B, in one embodiment, the base station 4 can have a generally "H" shaped base frame 5 that includes an elongate center support 6 having a length and opposing distal and proximal end portions each presenting a lateral support 7a,b. The base station 4 can optionally include an additional cross support 8 that can be positioned at an angle, e.g., orthogonally, along the center support 6, e.g., in middle of the center support. As shown in FIG. 1C, the base frame 5 can be further configured to receive and removably couple with components of the primary fixation device 1 such that the elongate base rail 2 is disposed substantially along the length of the base frame center support 6. As further depicted in FIG. 1C, an orthopedic fixation system 9 of the present invention can include the primary fixation device 1 removably coupled to the base station 4.

Figure 2A:
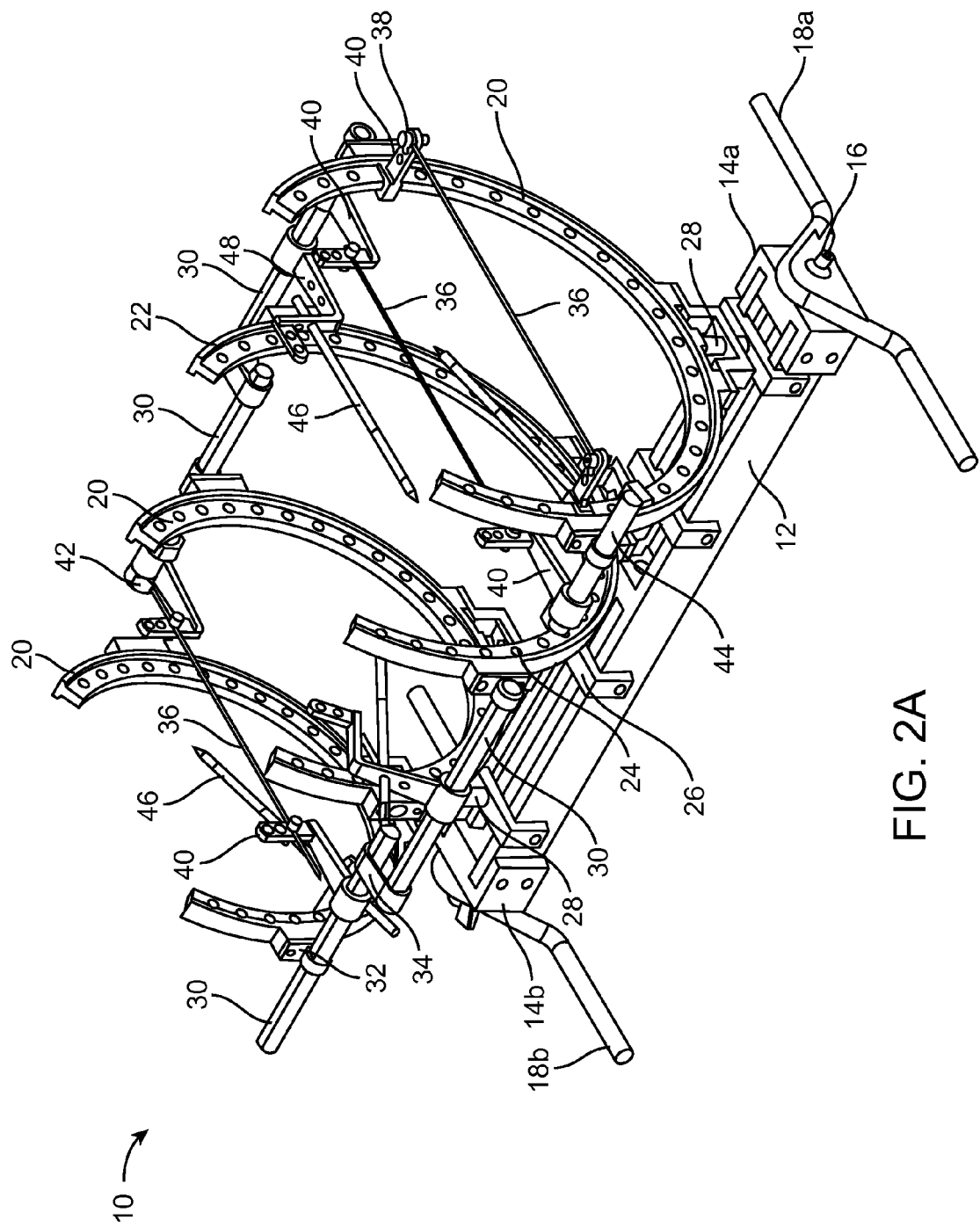
FIG. 2A illustrates a top-facing view of a primary fixation device, in accordance with an exemplary embodiment of the invention.
Figure 2B:
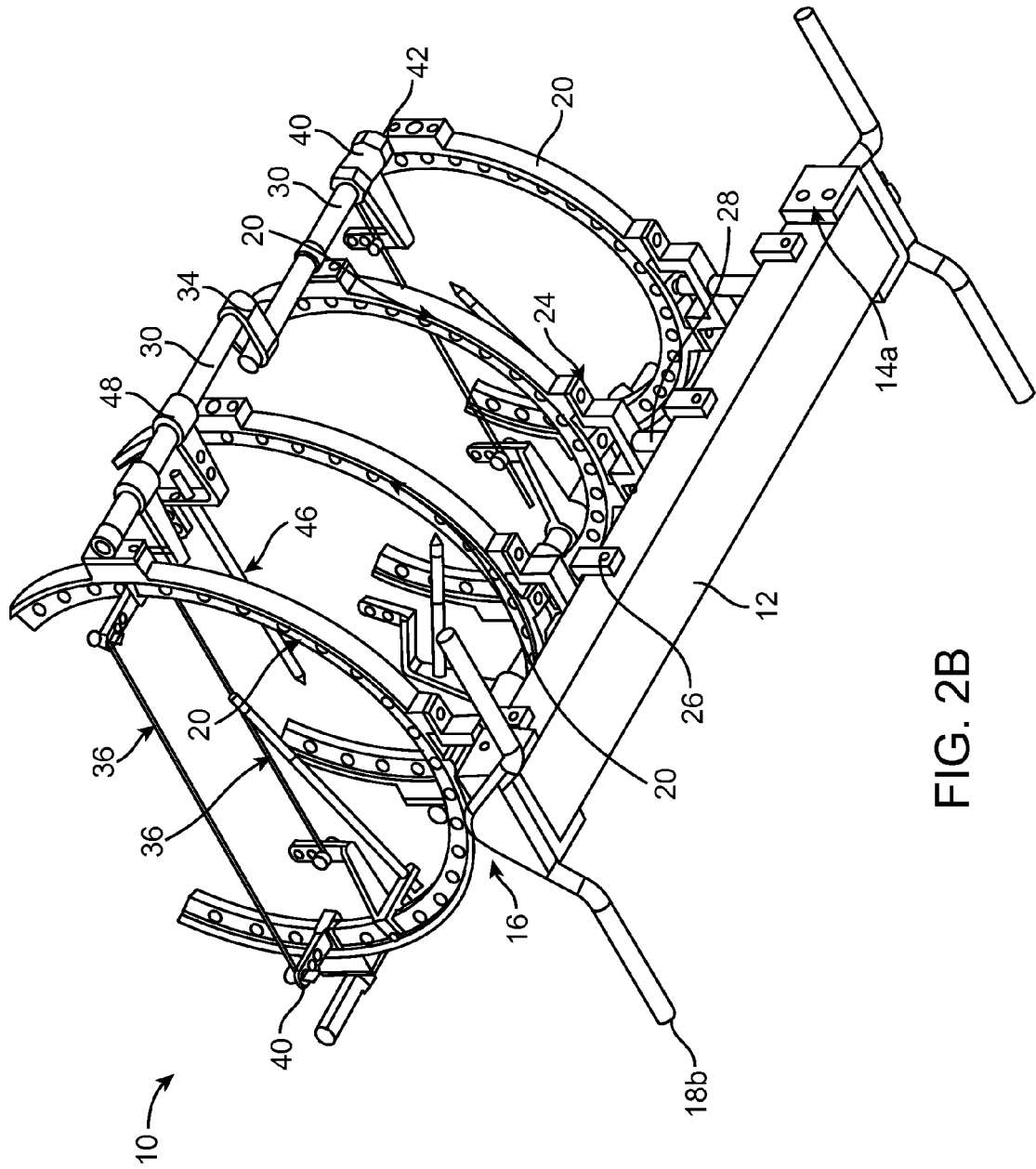
FIG. 2B shows a bottom-facing view of a primary fixation device, in accordance with an exemplary embodiment of the invention.

A primary fixation device according to an embodiment is illustrated with reference to FIGS. 2A and 2B. FIG. 2A illustrates a top-facing view and FIG. 2B illustrates a bottom-facing view of a primary fixation device 10 in accordance with an exemplary embodiment of the present invention. The primary fixation device 10 includes an elongate base rail 12 and a detachable base member 14a and 14b. In certain embodiments, the detachable base member 14a and 14b can be used to facilitate coupling a primary fixation device to a base station, as described below. The elongate base rail 12 has a length and opposing distal and proximal end portions, each removably couplable to a stand structure 18a and/or 18b. The stand structures 18a and 18b can be coupled at each end of the elongate base rail 12 with a fastener 16, and its relative dimensions to the elongate base rail 12 can, for example, can depend on the size of the limb being treated or the amount of support necessary for adequate stabilization. The primary fixation device 10 can include one or more rings 20 that can be selected to have the same or different shape and/or diameter. The rings 20 can include full rings and/or partial rings, such as half or three-quarter rings, and/or U-shaped plates. The rings 20 can also include holes 22 for coupling additional components to the rings 20. Each ring 20 can be removably and/or slidably coupled to the elongate base rail 12 along the base rail length, for example, by an adjustable height pedestal 24 that is coupled to a base block 26 with a post 28. The rings 20 can be further connected together with one or more struts 30 that can, for example, be configured to provide load-bearing support. A ring 20 can be attached to a strut 30 with a fastening member 32. The struts 30 can be further coupled together by a coupling member 34, which can, e.g., increase the stability of the device 10. At least one wire 36 can also be coupled to the device 10 by several ways to allow, e.g., for fixation of a bone. As shown in the exemplary embodiment, the wire 36 can be coupled with a bolt member 38 to a bracket 40, which can be coupled to a strut 30 and optionally held in place with a nut 42. Alternatively, the bracket 40 can be coupled to a ring 20. Also, a wire 36 can be coupled to a bracket 40, which can be coupled to an extension bar 44. In addition or in place of a wire 36, one or more fixing pins 46 can be included in the device 10. As shown, a fixing pin 46 can be coupled to a strut 30 by a flag member 48. It will be appreciated that coupling and positioning of the fixing pins 46 and/or wires 36 will depend on, for example, the type and size of the bone being treated and/or the location of the fracture.

Figure 3:
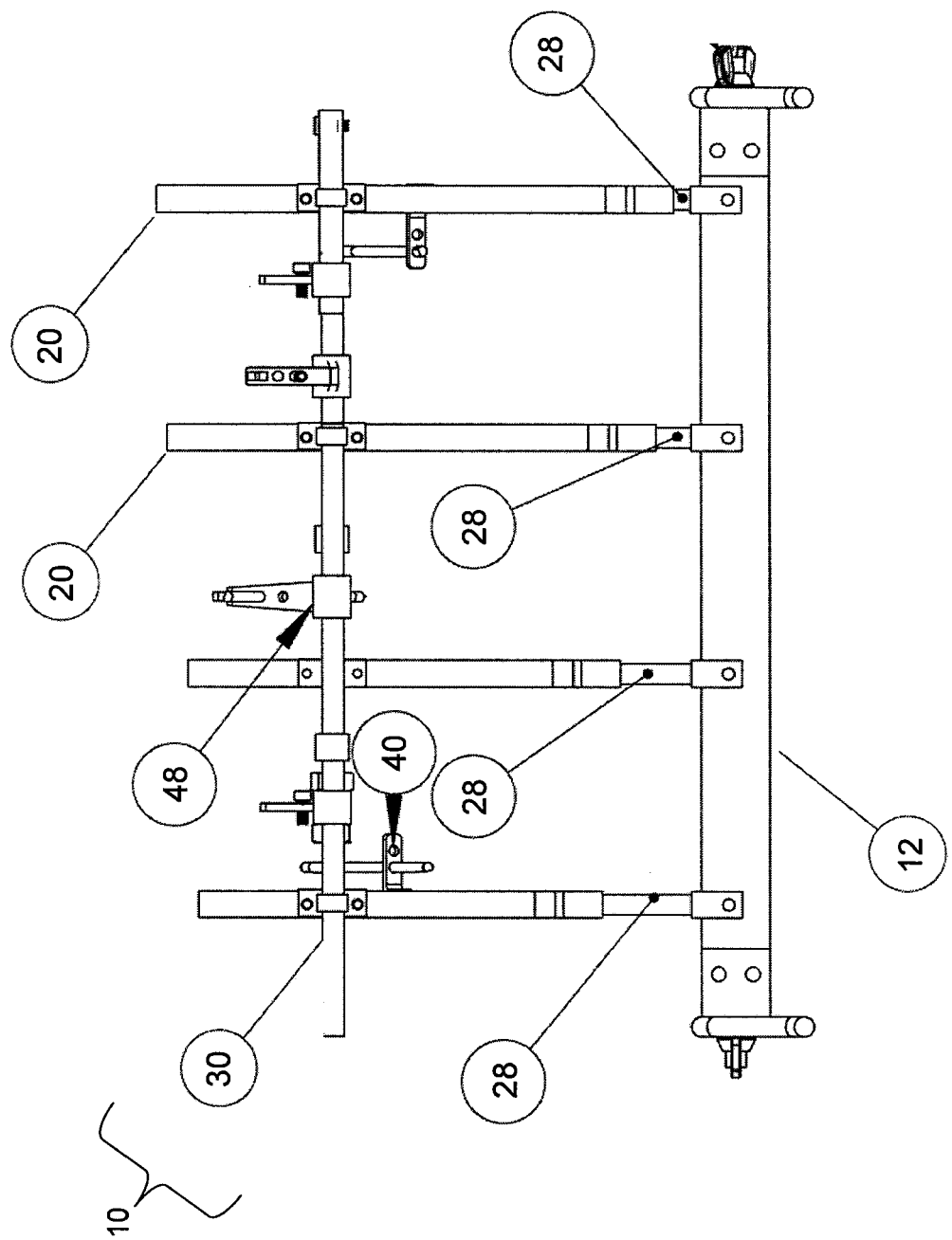
FIG. 3 shows a side view of a primary fixation device in accordance with an exemplary embodiment of the present invention.

FIG. 3 shows a side view of the primary fixation device 10 in accordance with an exemplary embodiment of the present invention. It is noted that the primary fixation device 10 can be configured to allow for increased adjustability that may be necessary for mobility and transport. As shown in this embodiment, the rings 20 of the device 10 can be positioned at different heights on the posts 28, which can be removably and slidably coupled to the elongate base rail 12. This height adjustability can further facilitate positioning of flag members 48 and/or brackets 40 in a straight line orientation, as shown by the orientation of the struts 30. In this embodiment, struts 30 can be positioned to be parallel to an axis along the length of the elongate base rail 12. Alternatively, the height can be adjusted to allow use of rings 20 with differing or the same diameters. For example, the diameters of the rings can decrease over the length of the elongate base rail 12 so as to allow for fixation of a limb having a decreasing diameter over its length, e.g., a leg. The rings 20 can also be positioned at a variety of angles relative to an axis along the length of the elongate base rail 12. As shown, the rings 20 are oriented orthogonally to the axis along the length of the elongate base rail 12.

Figure 4:
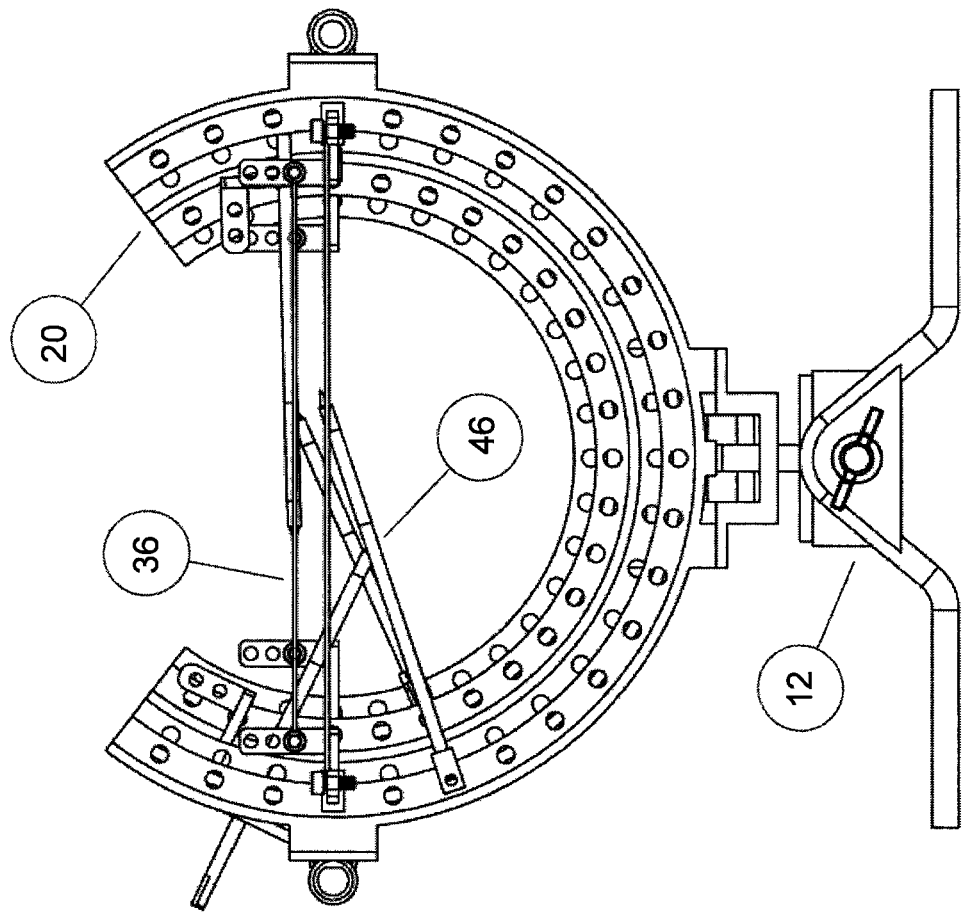
FIG. 4 illustrates a view down the length of a primary fixation device, according to an exemplary embodiment of the present invention.

FIG. 4 illustrates a view down the length of the primary fixation device 10 from one end of the elongate base rail 12, according to an exemplary embodiment of the present invention. As illustrated, the rings 20 can be positioned in seriatim down the axis of the elongate base rail 12. In addition, the fixing pins 46 and wires 36 can be positioned so as to intersect at a focal region near the center of the rings 20 that is typically located in the vicinity of a patient's limb placed in the assembly for stabilization. The position of each fixing pin 46 can be adjusted so as to allow for fixation of a bone of a patient within the rings 20 coupled to the elongate base rail 12.

Figure 5:
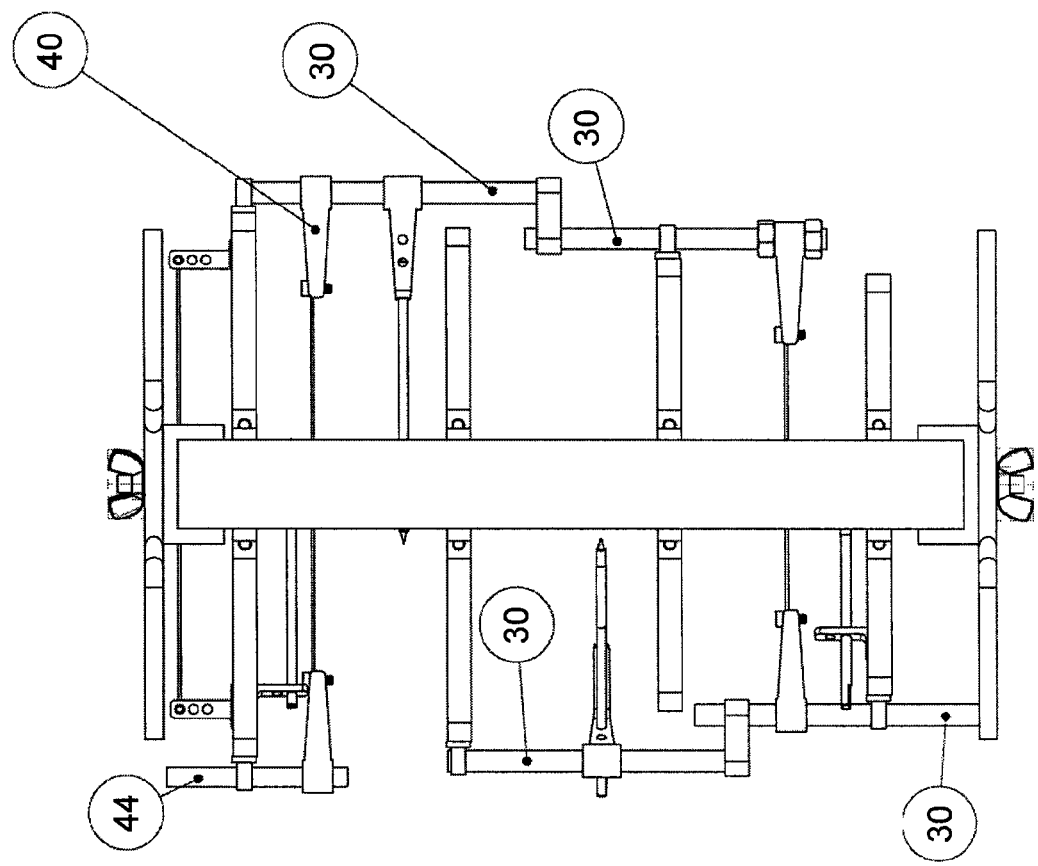
FIG. 5 shows a bottom view of a primary fixation device in accordance with an exemplary embodiment of the present invention.

FIG. 5 shows a bottom view of the primary fixation device 10 in accordance with an exemplary embodiment of the present invention. As shown, the struts 30 and the extension bar 44 can be positioned so as to be parallel to an axis along the length of the elongate base rail 12. The wires 36 and fixing pins 46 can be oriented in any angle that may be necessary to allow for fixation of the bone of the patient. For example, wires 36 coupled to brackets 40 can be positioned orthogonally to the struts 30. In addition, fixing pins 46 can also be positioned to be orthogonal to the axis along the length of the elongate base rail 12. It is also envisioned that each end of a wire 36 can be coupled to different rings 20 in the device 10.

In other embodiments, the present invention also provides orthopedic fixation systems including a primary fixation device and a base station. In some embodiments, the primary fixation devices can be transformed from a portable device to stationary devices by coupling to a base station configured to allow for increased stabilization of a bone of a patient. In certain embodiments, the primary fixation devices can be wholly or partially coupled with the base stations in a variety of ways. For example, a primary fixation device can be wholly coupled a base station such that all of the components in the primary fixation device are used upon incorporation into the base station. Alternatively, certain components and elements of the primary fixation device can be replaced with other components upon coupling with the base station. In an exemplary embodiment, the elongate base rail of a primary fixation device can be coupled to a base station including a generally "H" shaped base frame having an elongate center support having a length and opposing distal and proximal end portions each presenting a lateral support. The base frame can optionally include a support member that intersects the elongate center support at an angle, e.g., orthogonally, to provide additional stabilization to the assembly. In addition, rings of the primary fixation device can be coupled to one or more ring supports, which in turn can be coupled to one or more support members to provide for stabilization of a patient's limb.

Figure 6:
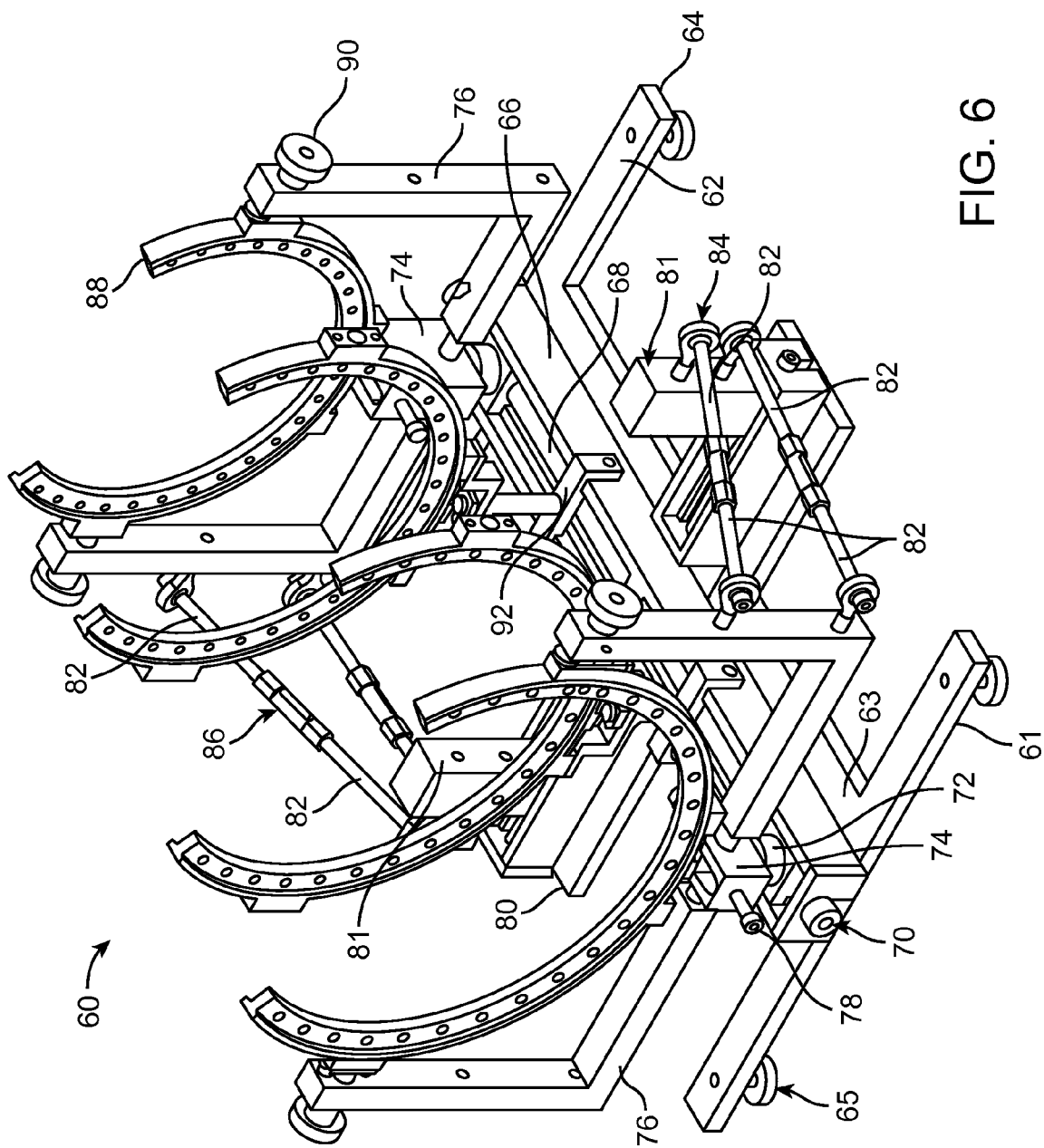
FIG. 6 illustrates a top-side view of an orthopedic fixation system in accordance with an exemplary embodiment of the invention.
Figure 7:
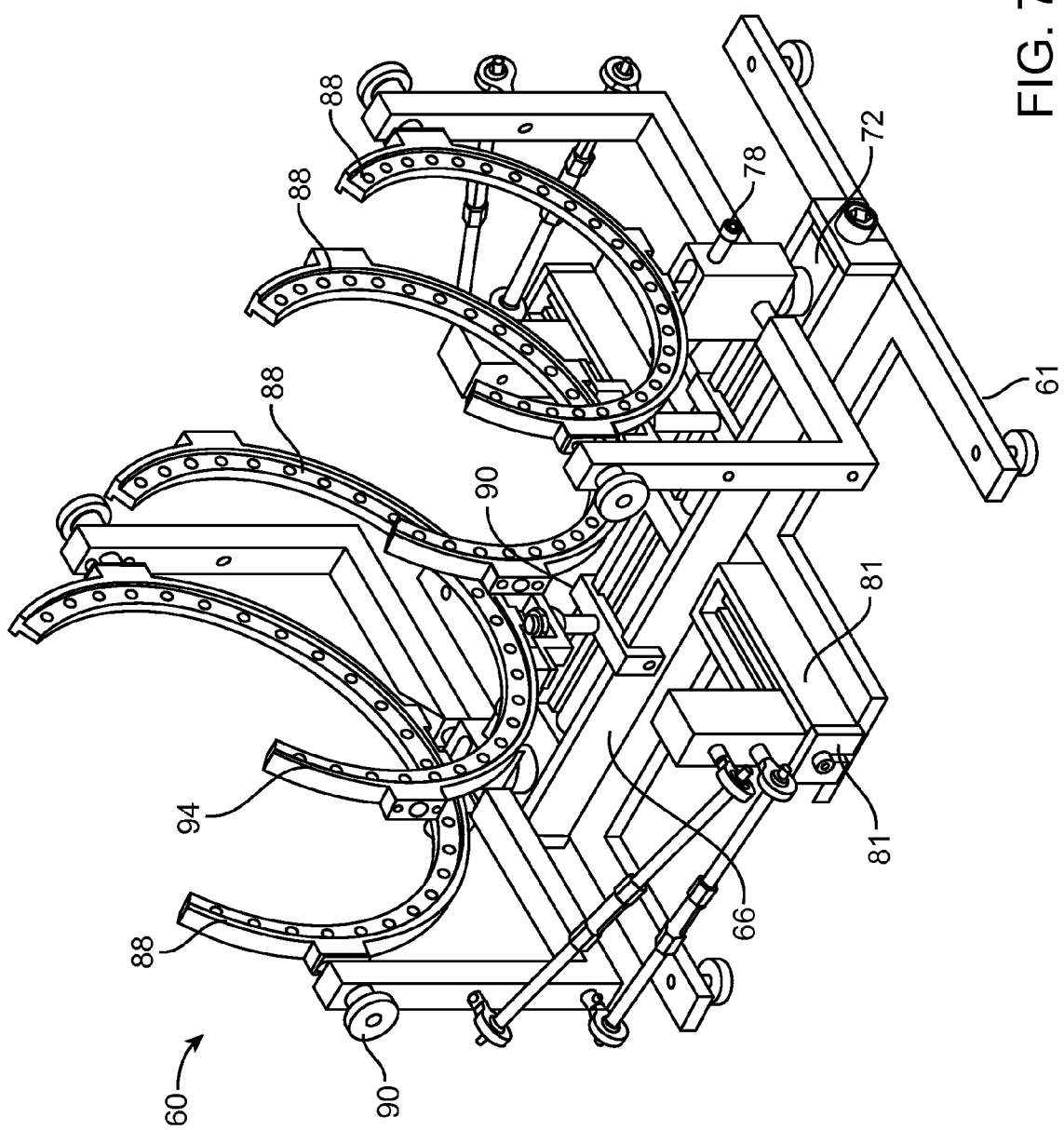
FIG. 7 illustrates another top-side view of an orthopedic fixation system in accordance with an exemplary embodiment of the invention.

FIGS. 6 and 7 illustrate different top-side views of an orthopedic fixation system 60 in accordance with an exemplary embodiment of the invention. The orthopedic fixation system 60 can include base station 61 having a generally "H" shaped base frame 62 comprising an elongate center support 63 having a length and opposing distal and proximal end portions each presenting a lateral support 64. The base station 61 can be adjusted with one or more leveling posts 65, e.g., coupled to each lateral support 64. As shown, certain components of the primary fixation device 10 (as described in more detail above) can be coupled to components of the base station 61. For example, an elongate base rail 66 (reference number 12, as described above) having a length can be coupled to the base station 61, which, for example, increases the stability of the assembly and allows for fixation in, e.g., an operating room. In certain embodiments, the elongate base rail 66 couples to the base station 61 having a generally "H" shaped base frame 62 that is configured to receive and removably couple with a primary fixation device 10 described above such that the elongate base rail 66 is disposed substantially along the length of the base frame center support 63. In some embodiments, the elongate base rail 66 can be composed of several different components. For example, the elongate base rail 66 can include a rod member 68 that is positioned along the center axis of the elongate base rail 66. The elongate base rail 66 can also include a fastening member 70 on one or both of opposing distal and proximal end portions of the elongate base rail 66. In certain embodiments, the fastening member 70 can replace the detachable base member 14 of the primary fixation device 10 described above. Additional components that can be replaced include one or more of the base blocks 26, posts 28, and adjustable height pedestals 24 described above. As shown, for example, the elongate base rail 66 can also include a bar-nut base 72 in the vicinity of the opposing distal and proximal end portions of the elongate base rail 66. A hinge base 74, which can be coupled to a ring support 76, can be coupled to the hinge base 74. The hinge base 74 can further include a tightening member 78. The ring support 76 can provide for additional stabilization and coupling to the base station 61. As shown, the base frame 62 can further include a cross support 80, which can be removably coupled with a support tower structure 81 that can be further coupled to one or more of the ring supports 76. In certain embodiments, a brace 82 can be coupled to the support tower structure 80 and/or to the ring support 76 by a coupling member 83. As shown here, a brace 82 can include rod supports 84 that can be adjusted relative to each other by an adjustment handle 84. The orthopedic fixation system 60 can further include one or more rings 88 that can be coupled to the ring support 76 with a fastener 90. Alternatively, one or more rings can be coupled to a base block 92, which is further coupled to the elongate base rail 66 similar to the embodiments discussed above for the primary fixation device 10. Similar to the exemplary embodiment in FIGS. 2A and 2B, additional fixing pins, wires, and other components can be coupled to the assembly 60 to facilitate treatment of a patient. For example, a bracket can be coupled to a hole 94 in a ring 88 to provide for coupling of a fixing pin or wire. In some embodiments, the orthopedic fixation system 60 can include the same fixing pins and/or wires that were inserted when the patient's bone was first reduced or fixed in the primary fixation device 10, described above.

Figure 8:
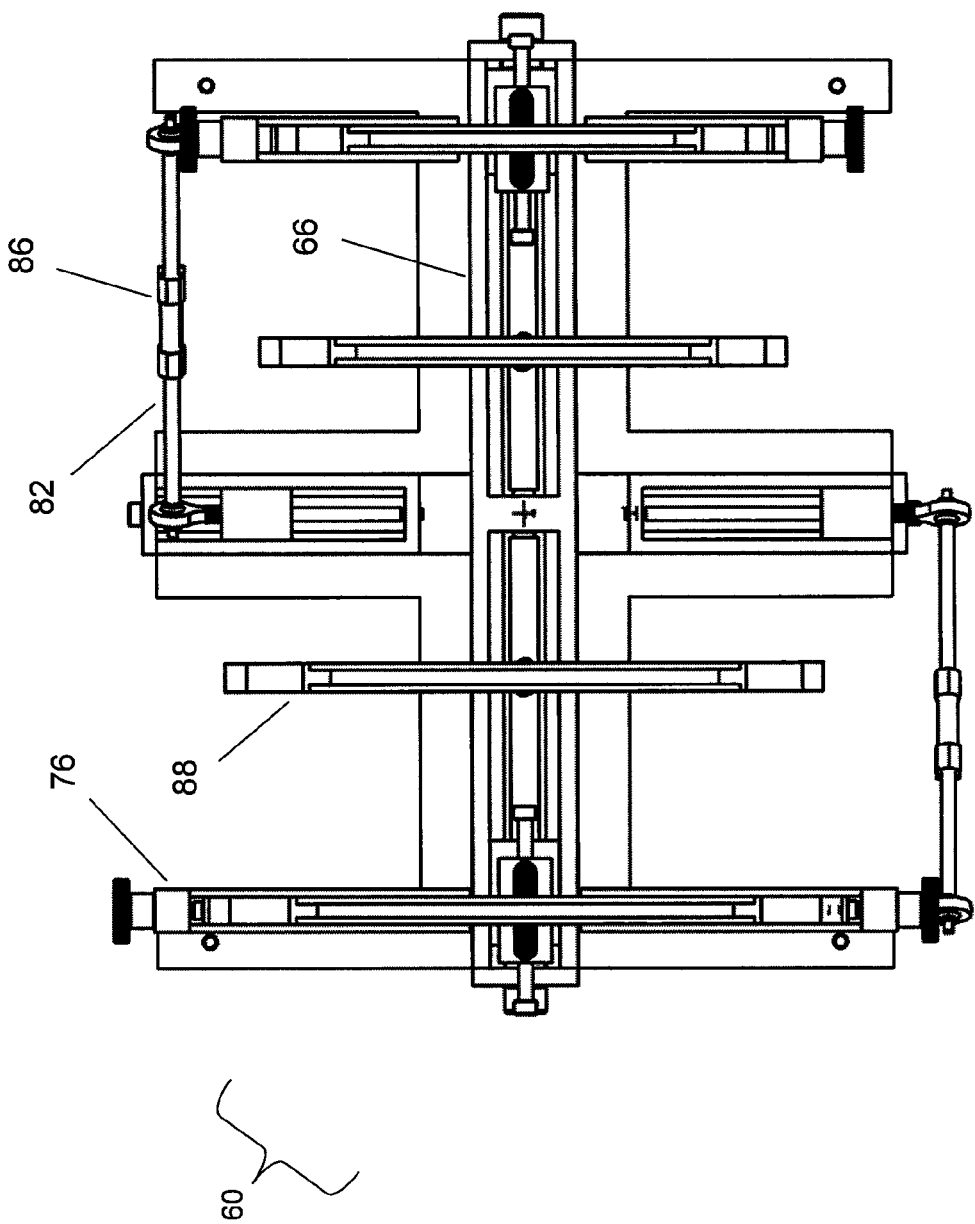
FIG. 8 shows a top view of an orthopedic fixation system in accordance with an exemplary embodiment of the invention.

FIG. 8 shows a top view of an orthopedic fixation system 60 in accordance with an exemplary embodiment of the invention. The various components of the assembly 60 can be positioned in a variety of angles and/or orientations, such as the orthogonal and/or parallel orientations shown. For example, the rings 88, the ring supports 76, and the cross support 80 can be orthogonal to an axis along the length of the elongate base rail 66. In this particular embodiment, the braces 82 are aligned to be parallel to the axis along the length of the elongate base rail 66. In addition, each brace 82 can be positioned on different sides of the base station 61 so as to provide additional cross support for stabilizing a patient's limb in the assembly 60.

Figure 9:
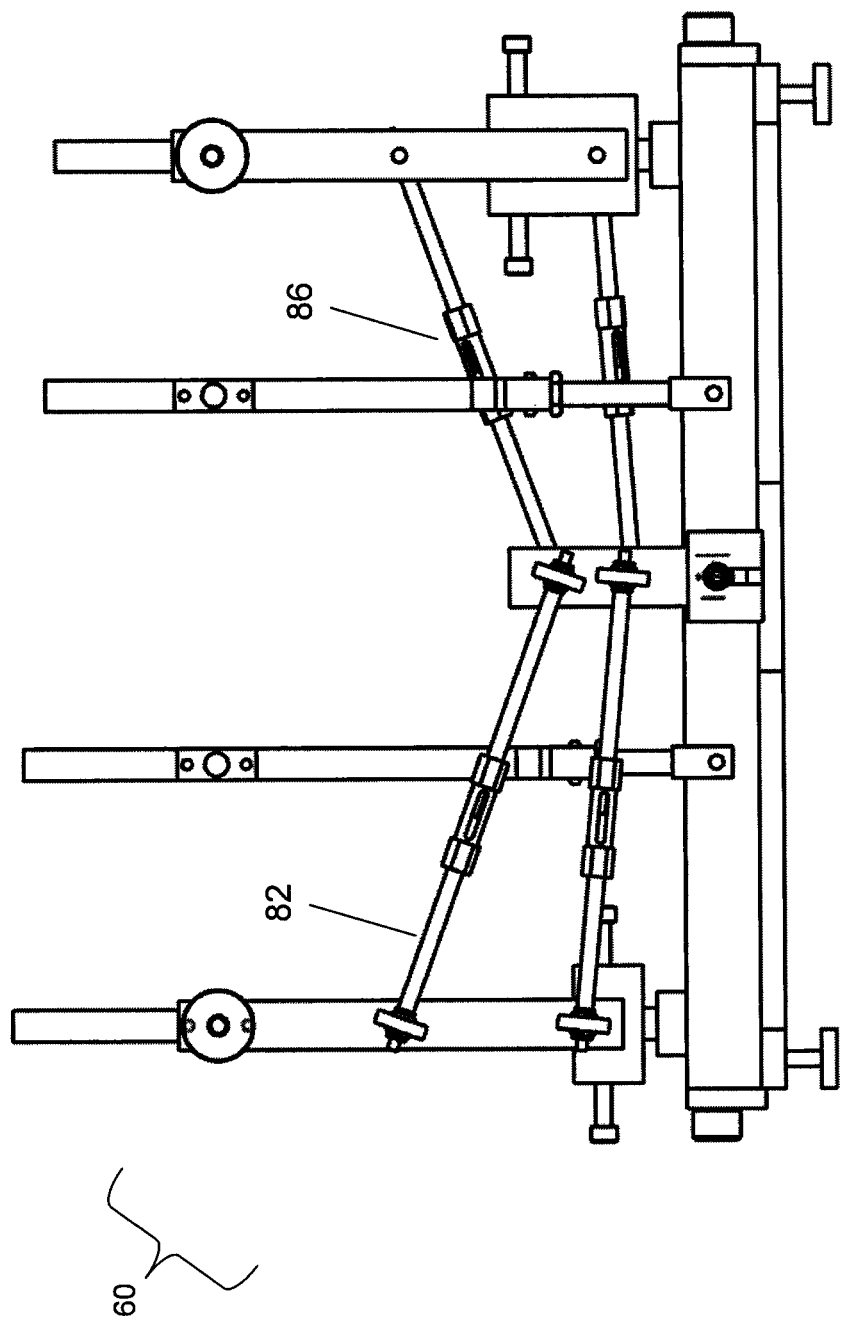
FIG. 9 illustrates a side view of an orthopedic fixation system in accordance with an exemplary embodiment of the invention.

FIG. 9 illustrates a side view of an orthopedic fixation system 60 in accordance with an exemplary embodiment of the invention. As shown, the cross support 80 can be positioned in a central location of the assembly 60, which will generally correspond to the placement of a patient's limb in the assembly 60. In addition, the braces 82 can be positioned at a variety of angles and heights. One of ordinary skill in the art will appreciate that positioning braces 82 can be arranged in a manner to provide maximum support to the assembly 60.

FIG. 10 illustrates a view down the length of the orthopedic fixation system 60 from one end of the elongate base rail 66, according to an exemplary embodiment of the present invention. As shown, the rings 88 can be positioned in seriatim down the length of the elongate base rail 66. The rings 88 can be selected to have a diameter so as to allow positioning of a limb in the central region of the rings 88. Wires and fixing pins, as provided e.g., in FIGS. 2A and 2B above, can then be positioned to allow for fixation of a limb during surgery. In some embodiments, the orthopedic fixation system 60 can include the same fixing pins and/or wires that were inserted when the patient's bone was first reduced or fixed in the primary fixation device 10 described above.

Structures, devices, and assemblies of the present invention will not be limited to any particular construction materials or compositions. Materials and compositions of the invention can include any variety of metals, alloys, polymers, and the like, alone or in combination, that are commonly used or generally suitable for use in medical or surgical applications. Extraction devices and components thereof may be made from conventional non-absorbable, biocompatible materials including stainless steel, titanium, alloys thereof, polymers, composites and the like and equivalents thereof.

In yet other embodiments, the present invention provides methods of using the devices and assemblies described herein. In an exemplary embodiment, the present invention provides a method of using an orthopedic fixation system can include transporting a patient from a first point to a second point while the patient's bone is immobilized with the primary fixation device and then coupling the primary fixation device to the base station at the second point while the patient's bone is immobilized with the primary fixation device. Other uses can include methods of using an orthopedic fixation system that include providing the orthopedic fixation system having a primary fixation device and a base station and coupling or uncoupling the primary fixation device and the base station while a bone of a patient is fixed or reduced with the primary fixation device. In yet other embodiments, a method of fixing or reducing a limb of a patient can include fixing or reducing a limb of a patient in a primary fixation device and coupling the primary fixation device to a base station while the patient's limb is constrained with the primary fixation device.

In yet another embodiment, the present invention provides a method for sterilizing a limb of a patient before an operation in which, for example, the primary fixation device is wholly or partially coupled together with the base station. In one embodiment, the present invention provides a method of sterilizing a limb of a patient positioned in an orthopedic fixation system that includes fixing or reducing the limb of the patient in a primary fixation device, placing a sterilizing container comprising a sterilization solution around the limb and the device, and removing the sterilization container such that the limb of the patient can be further stabilized by coupling the primary fixation device to a base station.

As illustrated in FIG. 11 A-C, the primary fixation devices of the present invention can be used for fixation and/or reduction of a patient's limb, e.g., a leg, under non-sterile conditions (FIG. 11A). As shown in FIG. 11B, a sterilizing container (e.g., a bag or other container providing sterilization conditions) can be placed around or in the vicinity of the patient's limb after temporary stabilization. The sterilizing container can be placed on or around the limb of the patient for a sufficient time period, such as the period between initial temporary stabilization until the patient arrives in an operating room for further treatment. After removal of the sterilizing container, the patient's limb can be positioned in a base station for treatment, such as for an operation (FIG. 11C). In certain embodiments, the orthopedic fixation systems of the present invention can further include a sterilization kit that can include a sterilizing container and a sterilization solution, such as, e.g., iodine, alcohol, or another liquid, gel, or other compound capable of sterilization.

One or more structures as described herein may be provided in the form of a kit. A kit may be assembled for portability, facilitating use in a surgical setting, and the like. This kit typically includes an orthopedic fixation system of the present invention, and the orthopedic fixation system may be provided in a fully assembled, partially assembled, or non-assembled configuration. As indicated, a device of the present invention may be configured or of a design that one or more components of the fracture reduction system have a limited or single use, or are replaceable. As such, a kit can include a fracture reduction device or assembly with one or more replacement components, such as one or more replacement primary fixation devices, base stations, or components thereof. A kit may include pre-sterilized components or device(s), as well as sterilized packaging.

The components of the present invention may be sterilized (and will generally be sterilizable) by any of the well known sterilization techniques, depending on the type of material. Suitable sterilization techniques include heat sterilization, radiation sterilization, chemical/gas sterilization, and the like.

The specific dimensions of any of the orthopedic fixation systems, assemblies, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. An orthopedic fixation system, comprising:
a primary fixation device comprising:
an elongate base rail having a fixed length and opposing distal and proximal end portions, the distal end portion of the base rail being removably couplable to a first base member and a separate first stand structure, such that the first base member is positioned between the distal end portion and the first stand structure, the proximal end portion of the base rail being removably couplable to a second base member and a separate second stand structure, such that the second base member is positioned between the proximal end portion and the second stand structure, the base rail having four substantially rectangular surfaces running along substantially the entire length of the base rail, the base rail comprising a generally round rod positioned along the center axis of the base rail; and a plurality of rings removably and slidably coupled through a window in one of the rectangular surfaces to the base rail along the base rail length, the plurality of rings including holes or ribs removably coupled to at least one bone-interface component configured for fixing to a bone of a patient; and at least two struts removably mechanically coupling together at least two of the plurality of rings independently of the base rail, the two struts being separate and distinct from the elongate base rail;

wherein the elongate base rail with the attached first base member, first stand structure, second base member and second stand structure has a generally H shape, wherein the first stand structure and the second stand structure provide support to the primary fixation device.

2. The orthopedic fixation system of claim 1, further comprising a sterilization kit.

3. The orthopedic fixation system of claim 2, wherein the sterilization kit comprises a sterilizing container, a sterilization solution, or a combination thereof.

4. The orthopedic fixation system of claim 1, wherein the system is a reduction device for the bone of the patient.

5. The orthopedic fixation system of claim 1, wherein the at least one bone-interface component comprises at least one fixing pin, at least one wire, or a combination thereof.

6. The orthopedic fixation system of claim 5, wherein the at least one fixing pin and the at least one wire are independently and removably coupled to at least one ring of the plurality of rings.

* * * * *